(12) United States Patent
Beaubien (10) Patent No.: US 9,725,229 B2
(45) Date of Patent: Aug. 8, 2017

(54) DEVICES AND METHODS FOR APPLYING BODY LOTIONS SUCH AS SUNSCREENS

(71) Applicant: Barry Beaubien, Howell, MI (US)

(72) Inventor: Barry Beaubien, Howell, MI (US)

(*) Notice: Subject to any disclaimer, the term of this patent is extended or adjusted under 35 U.S.C. 154(b) by 146 days.

(21) Appl. No.: 14/475,939

(22) Filed: Sep. 3, 2014

(65) Prior Publication Data

US 2015/0063892 A1 Mar. 5, 2015

Related U.S. Application Data

(60) Provisional application No. 61/873,050, filed on Sep. 3, 2013.

(51) Int. Cl.
  *B65D 83/08* (2006.01)
  *A61M 35/00* (2006.01)

(52) U.S. Cl.
  CPC ......... *B65D 83/0894* (2013.01); *A61M 35/00* (2013.01); *A45D 2200/1081* (2013.01)

(58) Field of Classification Search
  CPC combination set(s) only.
  See application file for complete search history.

(56) References Cited

U.S. PATENT DOCUMENTS

| | | | | |
|---|---|---|---|---|
| 4,150,904 A | * | 4/1979 | Stewart | B05C 17/0205 |
| | | | | 401/186 |
| 4,759,652 A | * | 7/1988 | Ulrich | A45D 34/00 |
| | | | | 15/222 |
| 5,013,171 A | * | 5/1991 | Almond, II | A47K 7/022 |
| | | | | 15/222 |
| D333,191 S | | 2/1993 | Rainen | |
| 5,660,636 A | * | 8/1997 | Shangold | A47K 10/32 |
| | | | | 118/419 |
| 5,851,077 A | | 12/1998 | Trejo | |
| 6,017,162 A | | 1/2000 | Call | |
| 6,382,552 B1 | * | 5/2002 | Paul | A47K 10/3827 |
| | | | | 242/594.5 |
| 6,530,707 B1 | | 3/2003 | Byrne et al. | |

(Continued)

FOREIGN PATENT DOCUMENTS

| | | |
|---|---|---|
| EP | 0891725 | 1/1999 |
| EP | 2206447 | 7/2010 |

OTHER PUBLICATIONS

English translation of abstract for EP2206447.
English translation of abstract for EP0891725.

*Primary Examiner* — David Walczak
(74) *Attorney, Agent, or Firm* — Dinsmore & Shohl LLP (57) ABSTRACT

Hand-held articles for applying lotion to a user, including a user's back or other hard-to-reach places. A housing contains a lotion to be dispensed, and a member, integral to the housing, transfers the lotion to a user's body. The member may be a roller or a pre-moistened, elongated sheet, web or strip, with the housing containing a roll of pre-moistened material. The housing may further include a manually operated lever that allows a length of the strip to be pulled from the roll in the housing. The housing may additionally include a cap with a cutting edge to sever the strip at a desired length. The strip of material may be pre-moistened with a tanning lotion; self-tanning lotions; sun block; moisturizing cream, or insect repellant. The strip of material may be made of a non-woven synthetic fibrous material, with a width in the range of 1 to 3 inches.

6 Claims, 6 Drawing Sheets

(56) References Cited

U.S. PATENT DOCUMENTS

| | | |
|---|---|---|
| 6,607,514 B2 | 8/2003 | Reese |
| 6,899,481 B2 * | 5/2005 | Katsandres ............ A45D 34/04 15/222 |
| 7,044,670 B2 | 5/2006 | Delage |
| 7,101,106 B1 * | 9/2006 | Wiley ................. A45D 34/041 401/205 |
| D663,479 S | 7/2012 | Ammerman |
| 2012/0282199 A1 | 11/2012 | Pollack et al. |

\* cited by examiner

DEVICES AND METHODS FOR APPLYING BODY LOTIONS SUCH AS SUNSCREENS

REFERENCE TO RELATED APPLICATION

This application claims priority from U.S. Provisional Patent Application Ser. No. 61/873,050, filed Sep. 3, 2013, the entire content of which is incorporated herein by reference.

FIELD OF THE INVENTION

This invention relates generally to lotion dispensers and, in particular, to devices and methods for applying lotions such as sunscreens.

BACKGROUND OF THE INVENTION

There are many occasions wherein an individual desires to apply a body lotion prior to a trip to the beach or a session at a tanning salon, but the applicator choices are limited. At a tanning salon, it would be advantageous to provide one-time or disposable applicators so that a user need not purchase or bring a large bottle of lotion. Further, whether at the salon or the beach, it would be advantageous if the device and method enabled a user to apply lotion to their own back area without having to enlist the assistance of others.

There are many devices and inventions relating to applying lotions and the like to one's back with the aid of another. Such devices include long-handled rollers and other implements. Some devices use strips of material. U.S. Pat. No. 6,607,514, for example, discloses an applicator system for storage and retrieval of applicator strips from a container to be used for applying a liquid preparation to a user's body. An elongated applicator strip is hand held for the user to apply the liquid preparation on remote body parts, such as the back. The applicator strips can be sealed in the container to prevent the evaporation of the liquid preparation contained therein. The applicator strips have laminated layers including an absorbent first layer to receive and retain the liquid preparation. A non-absorbent stabilizing second layer is included to provide strength and dimensional stability. Preferably, the strip includes two outer first layers and one middle second layer. Each elongated applicator strip is preferably about 36 inches in length and about 4.5 inches in width.

SUMMARY OF THE INVENTION

The invention resides in a hand-held article for applying lotion to a user, including a user's back or other hard-to-reach places. In broad and general terms, the article includes a housing containing a lotion to be dispensed, and a member, integral to the housing, for transferring the lotion to a user's body. The member may be a roller, in which case the dispenser may be an elongated wand or an existing lotion bottle having threads to which the roller attaches.

In the preferred embodiment, the member is a pre-moistened, elongated sheet, web or strip, with the housing containing a roll of pre-moistened material. The housing may further include a manually operated lever that allows a length of the strip to be pulled from the roll in the housing. The housing may additionally include a cap with a cutting edge to sever the strip at a desired length. Optionally, the housing includes a tensioning mechanism to keep excess material from coming off the roll, and/or a separately fillable lotion reservoir.

A particular article for applying lotion to a user comprises a housing containing an elongated strip of material on a roll internal to the housing, the strip being pre-moistened with a lotion. The housing includes a slot through which the strip is pulled off of the roll and out of the housing. A manually operated lever, proximate to the slot, has a first position enabling the strip to be pulled off of the roll and out of the housing, and a second position preventing the strip to be pulled off of the roll and out of the housing. A cap is provided with an integral cutting edge to sever the strip at a desired length once pulled off of the roll and out of the housing. The housing may further includes a tensioning mechanism to keep excess material from coming off the roll, and/or a separately fillable lotion reservoir.

The strip of material may be pre-moistened with a tanning lotion; self-tanning lotions; sun block; moisturizing cream, or insect repellant. The strip of material may be made of a non-woven synthetic fibrous material, with a width in the range of 1 to 3 inches. The strip of material more preferably has a width in the range of 2 to 2.5 inches.

DETAILED DESCRIPTION OF THE PREFERRED EMBODIMENTS

Figures 1, 2, 3:
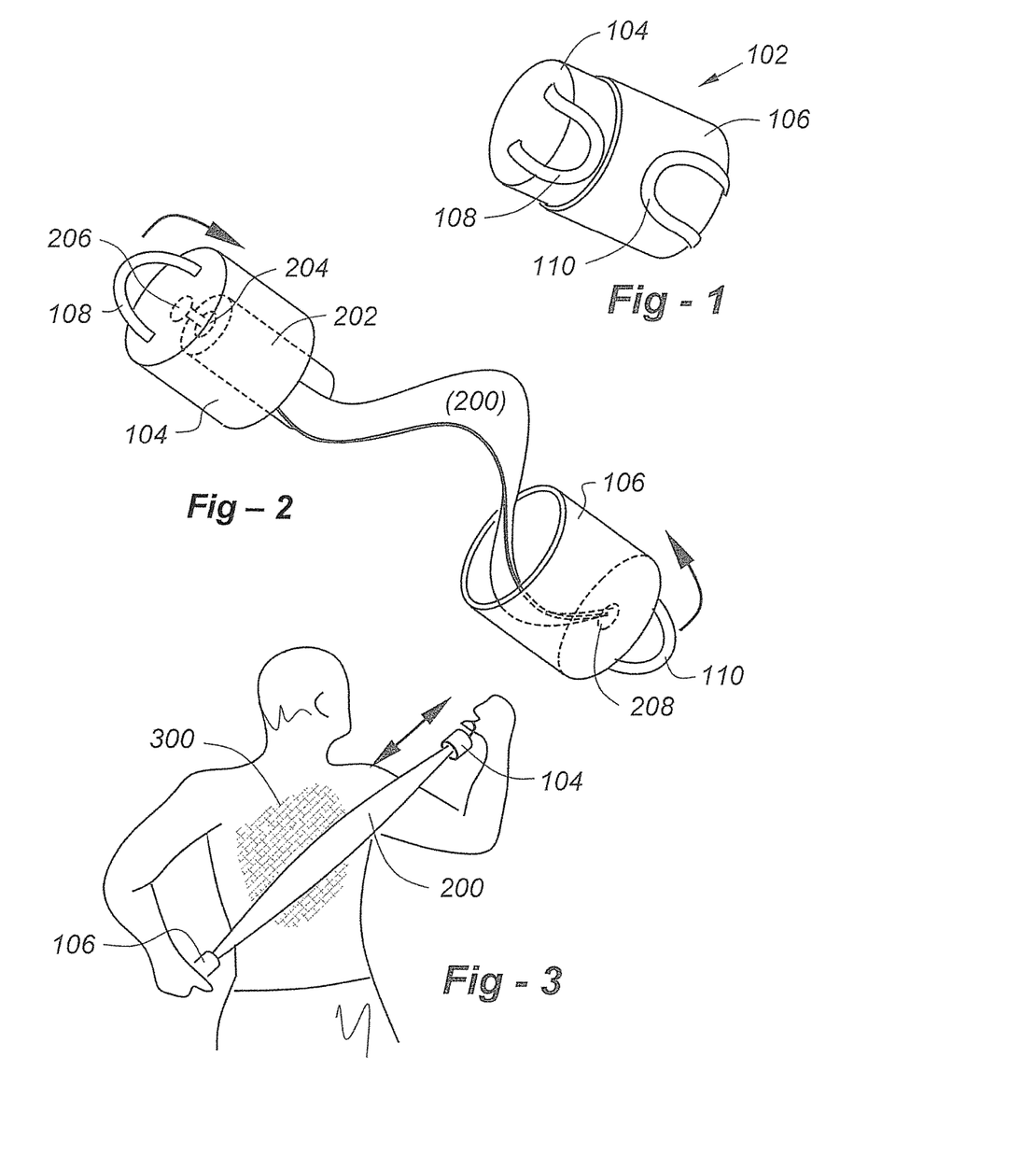
FIG. 1 is a drawing of a first embodiment of the invention in the form of a small, cylindrical article with two portions that come apart by pulling on handles.
FIG. 2 shows the two halves of the article of FIG. 1 initially pulled apart.
FIG. 3 illustrates that when the two halves of the article of FIG. 2 are pulled apart, the system enables a user to apply any type of lotion or liquid to areas of their back which they may otherwise be unable to reach.

This invention solves the above problems by providing lotion applicators for different purposes at low cost. FIG. 1 is a drawing of a first embodiment of the invention in the form of a small, cylindrical article 102 with two portions 104, 106 that come apart by pulling on handles 108, 110. The handles may be folded down onto the sides of the article until use, and all aspects may be made of disposable materials such as cardboard, plastic, and paper.

FIG. 2 shows the two halves 104, 106 initially pulled apart. Inside, a pre-moistened paper or other material 200 comes off of roll 202 which is rotatable about pin 204 that extends through the end of the housing, held in position with button 206. The other end of the applicator may be anchored at 208 to the inner wall of the other portion 106.

As shown in FIG. 3, when the two halves are pulled apart, the system enables a user to apply any type of lotion or liquid to areas 300 of their back which they may otherwise be unable to reach.

Figures 4A, 4B:
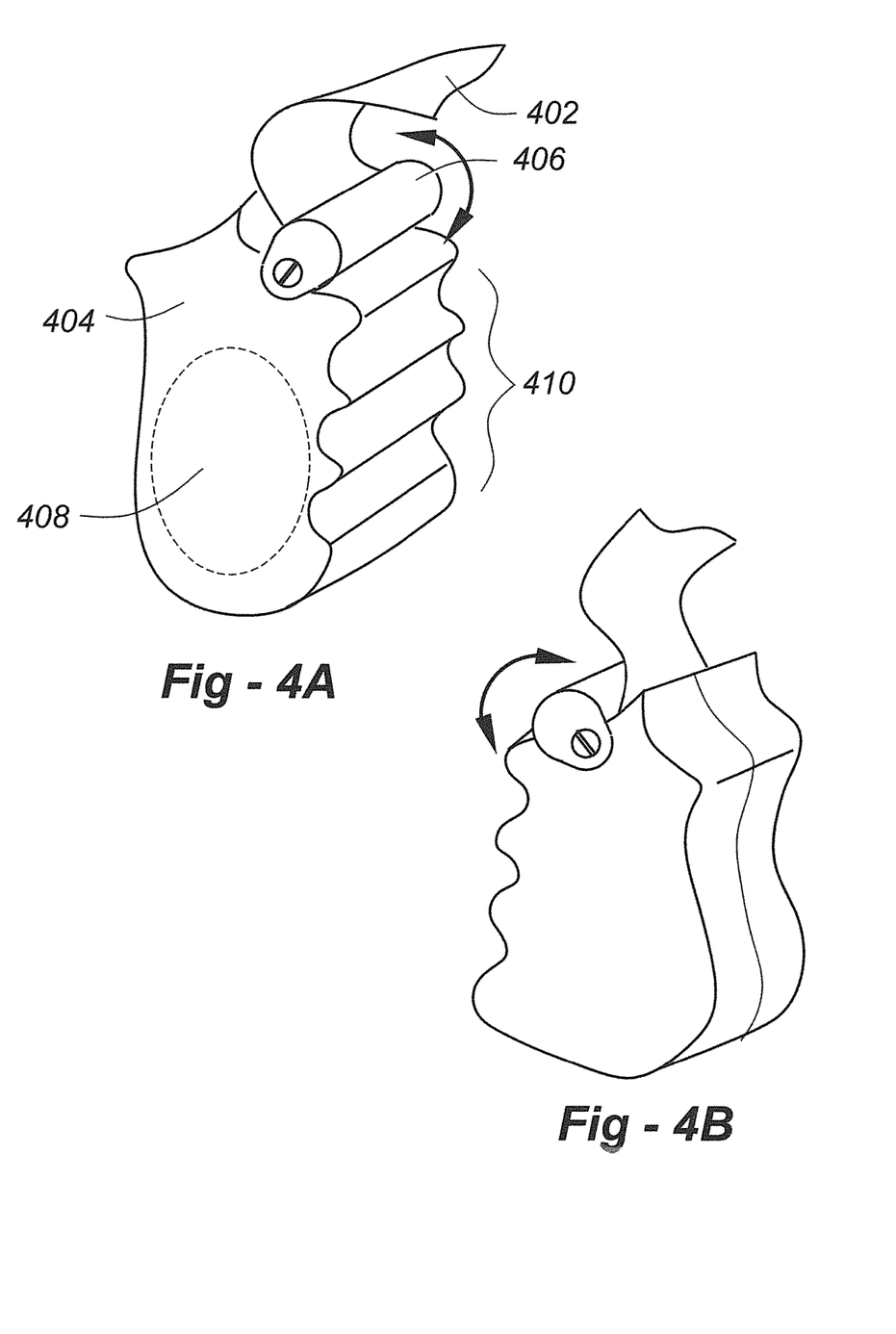
FIG. 4A is an oblique drawing of a different dispenser according to the invention, wherein a much longer applicator strip is contained in a decorative housing.
FIG. 4B shows the back of the item of FIG. 4A.

FIG. 4A is an oblique drawing of a different dispenser according to the invention, wherein a much longer applicator strip 402 is contained in a roll within housing 404. FIG. 4B shows the back of the item. This system includes a pivoting bar-like member 406 which pivots as shown to allow (and prevent) the strip, which again is pre-moistened, to come off internal roll 408. The pivoting bar-like member 406 may include a surface that provides friction when engaged against the pre-moistened strip, and the dispenser or member 406 may include a serrated tear-bar enabling the strip to be torn off at a desired length for use.

Thus, in operation, a user grasps the dispenser with one hand using finger depressions 410, while grasping the free end of the strip 402. The strip can then either be torn from the dispenser and used by itself, or the user may continue to hold the dispenser, tearing the strip off following use. An optional spout may be provided to extract additional fluid for independent application.

Figure 4C:
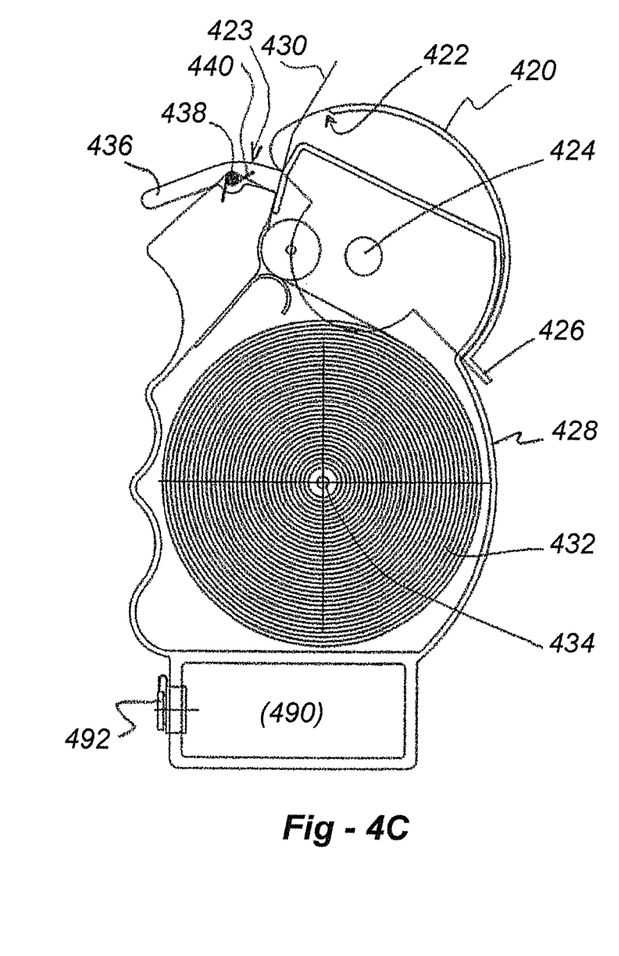
FIG. 4C is a cross sectional drawing of a device like the one depicted in FIGS. 4A, B, but with additional features including a cover with integral cutter and a lotion reservoir.

FIG. 4C is a cross sectional drawing of a device like the one depicted in FIGS. 4A, B, but with additional features includes a cover 420 with integral cutter and a lotion reservoir 490. The cover pivots on axis 424, and the cover is shown in an open configuration having been pivoted clockwise until stop 426 hits the outer surface of the housing 428, enabling premoistened strip 430 to be drawn from the device. To release the strip from the roll 432, which rotates on axis 434, a user depresses lever 436 which pivots on axis 438. Pressing the lever 436 works against a spring 440, causing the end 442 to move away from a surface 444, as shown in the detail drawing of FIG. 4D. One or both of the surfaces 442, 444 may me serrated or otherwise roughened to ensure that the strip does not slip when lever 436 is not pressed.

Figure 4D:
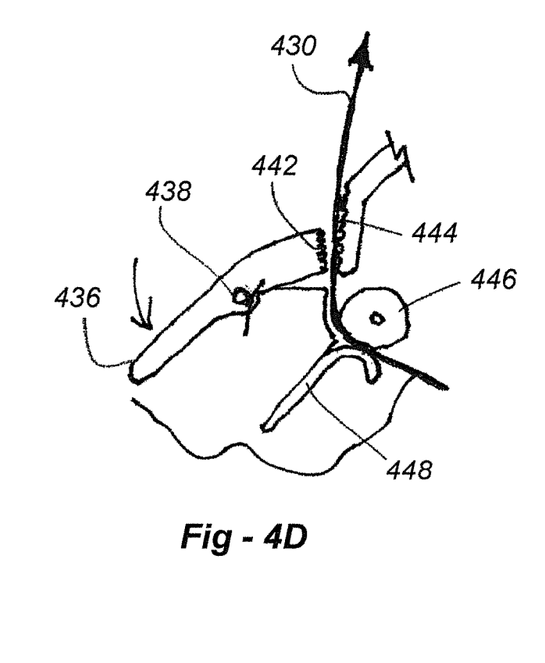
FIG. 4D is a detail drawing that better illustrates a lever release mechanism.

FIGS. 4C and 4D both illustrate an optional yet preferred tensioning mechanism comprising roller 446 and tensioning spring 448. In use, as the strip 430 is pulled out of the housing, it rolls on the surface of roller 446 and past spring 448 which is urged against the roller 446. This added resistance to pull ensures that excessive material is not pulled off roll 432 which might interfere with the operational mechanism. When a desired length of strip 430 has been released, cover 420 may be closed, causing cutter 422 to but up against surface 423 to cut the strip to length. Optional but desirable lotion reservoir 490 is filled and refillable via capped port 492.

As with other embodiments disclosed herein, the device of FIGS. 4C and 4D is constructed largely of molded plastic, with the exception of the spring(s) which may be metal. The strip of material 430 is preferably made of an inexpensive yet strong and absorbent natural or synthetic material. A non-woven fibrous cellulosic or synthetic material such as PET or polypropylene may be used. Biodegradable and/or recycled materials may also be used. Non-woven technologies include spun-bonded, felted and needle-punched. The strip is preferably non-perforated so that it does not break unintentionally. Multi-layer strips may be used; for example, with a strong backing layer bonded to one or more absorbent layers. The width of the strip is preferably on the order of 1 to 3 inches, more preferably in the range of 2 to 2½ inches.

The housings of the invention such as the one depicted in FIG. 4C comes with a roll of the strip material, pre-moistened with any of a number of formulations, including tanning self-tanning lotions, sun blocks, moisturizing creams, insect repellants, and the like. The invention is not limited in this regard. If lotion reservoir is provided, it need not have the same liquid as the strip. For example, the strip may be pre-moistened with a sunblock, while the reservoir contains moisture cream.

Roller Embodiments

Figure 5A:
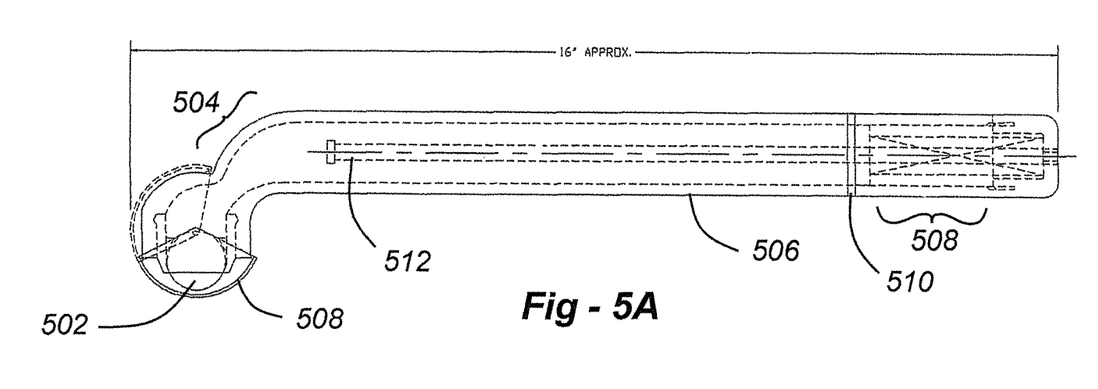
FIG. 5A illustrates an alternative embodiment of the invention, wherein a roller is supported in an elongated housing having a bent neck portion.
Figure 5B:
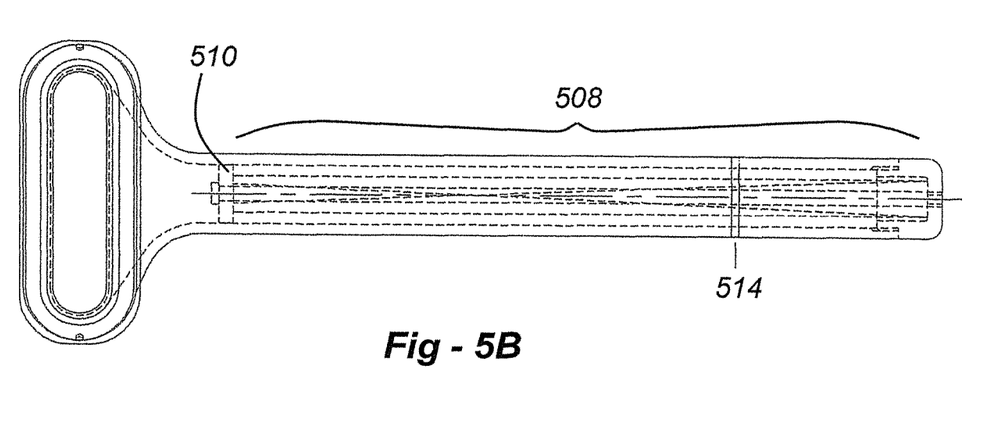
FIG. 5B is a bottom view of the device of FIG. 5A.
Figure 5C:
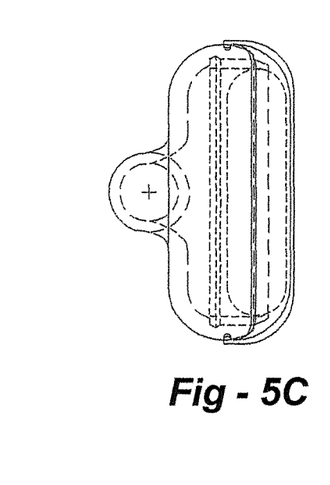
FIG. 5C is a front view of the device of FIG. 5A.

Apart from the pre-moistened strip embodiments of the invention described above, other embodiments use a roller in communication with a lotion supply. FIGS. 5A-5C illustrate one such device, wherein a roller 502 is supported in an elongated housing 506 having a bent neck portion 504. FIG. 5A is a side view of the device, FIG. 5B is a bottom view, and FIG. 5C is a front view.

A guard piece 508 may be provided to protect the roller 502 when not in use. Such guard piece may be removable or attached and pivotable between retracted and non-retracted positions. Any desired lotion would be added to the handle 506, which would be delivered to the body of a user through roller 502. The length of the handle portion 506 would preferably be long enough (i.e., 12-20 inches) to enable a user to reach the middle of their back. The broken lines in FIGS. 5A-5C indicate internal structure of some embodiments. For example, the broken lines at 508 may indicate a spring that pushes a plunger 510 against the lotion contained in the housing 506. A central guide rod 512 may be provided for the plunger to travel along. A band or window of clear plastic may be provided, as show at 514, to indicate when the housing is full.

Figure 5D:
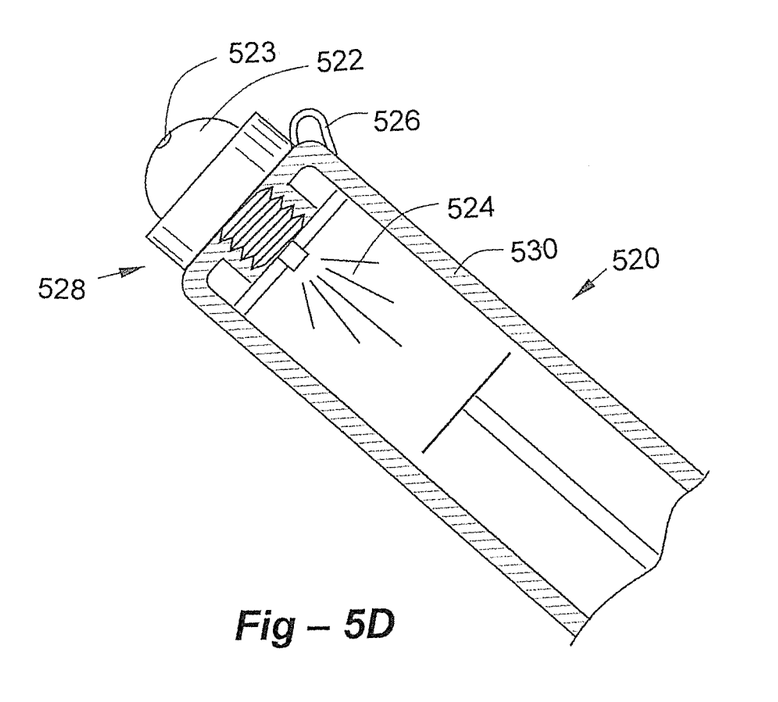
FIG. 5D shows a manual pump mechanism that may be included in the end of the housing of FIGS. 5A and 5B.

FIG. 5D shows a manual pump mechanism that may be included in the end of the housing 506 of FIGS. 5A and 5B. The mechanism, depicted at 520, includes a depressible 'bulb' 522 which operates when a user covers the hole 523 with the thumb for example and pumps the bulb 522, pressurizing the internal cavity of the housing with air shown at 524. The user would grip the outer surface of the container at 530. Item 526 is an optional molded strap to keep cap assembly 528 from falling out during refills.

Figure 6:
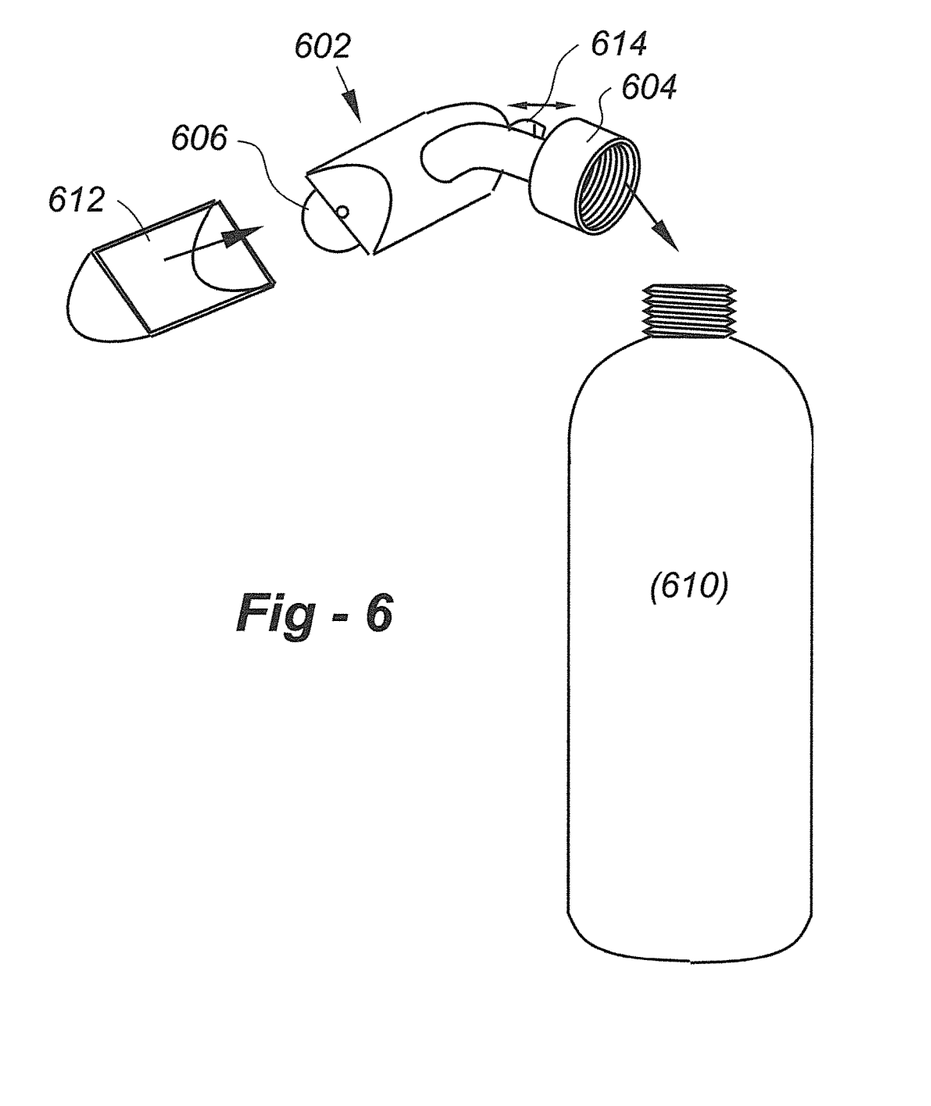
FIG. 6 shows a roller portion with a threaded end enabling the roller portion to be coupled to an existing bottle of lotion.

As opposed to an integrated assembly, another embodiment of the invention includes only the roller portion 602 with a threaded end 604 enabling the roller portion to be coupled to an existing bottle of lotion 610, as shown in FIG. 6. Again, a snap-on/off cover guard 612 may be provided. The neck portion may be curved and may be of any convenient length, and a sliding button 614 may be provided to block the flow of liquid to the roller 606 when not in use. In an alternative embodiment, roller 602 may be augmented or replaced with retractable strip of pre-moistened material enabling the strap to be extended for application and drawn back up between uses.

The invention claimed is:

1. A disposable article for applying lotion to a user, comprising:
  a housing containing an elongated strip of material on a roll internal to the housing, the strip being pre-moistened with a lotion;
  the housing being constructed of a first portion having a cylindrical sidewall, a closed end wall and an open opposite end wall containing the roll of the material, and a second portion having a cylindrical sidewall, a closed end wall and an open opposite end wall to which an end of the elongated strip of material is attached, the first portion open end wall being received into the second portion open end wall such that the second portion surrounds at least part of the first portion in a nested configuration;

wherein the two portions of the housing pull apart, enabling the strip of material to be pulled off of the roll and out of the housing such that the strip of material and lotion may be applied to a user's back while holding the first and second portions of the housing in opposite hands.

2. The article of claim 1, wherein the strip of material is pre-moistened with one or more of the following:

tanning lotion;
self-tanning lotions;
sun blocks;
moisturizing creams, and insect repellant.

3. The article of claim 1, wherein the strip of material is made of a non-woven synthetic fibrous material.

4. The article of claim 1, wherein the strip of material has a width in the range of 1 to 3 inches.

5. The article of claim 1, wherein the strip of material has a width in the range of 2 to 2.5 inches.

6. The article of claim 1, wherein the two portions each include a handle to assist in pulling the portions apart the handles each folding against a side of the respective portion until used to pull the portions apart.

* * * * *